United States Patent [19]
Lizardi et al.

[11] Patent Number: 5,312,728
[45] Date of Patent: May 17, 1994

[54] ASSAYS AND KITS INCORPORATING NUCLEIC ACID PROBES CONTAINING IMPROVED MOLECULAR SWITCH

[75] Inventors: Paul M. Lizardi, Cuernavaca, Mexico; Fred R. Kramer, New York, N.Y.; Sanjay Tyagi, New York, N.Y.; Cesar E. Guerra, New York, N.Y.; Hilda M. L. Buyoli, Col Marte, Mexico; Barbara C. Chu, Del Mar, Calif.; Gerald F. Joyce, Encinitas, Calif.; Leslie E. Orgel, La Jolla, Calif.

[73] Assignees: Public Health Research Institute of the City of New York, Inc., New York, N.Y.; The Salk Institute for Biological Studies, San Diego, Calif.

[21] Appl. No.: 878,230

[22] Filed: May 4, 1992

Related U.S. Application Data

[62] Division of Ser. No. 251,696, Sep. 30, 1988, Pat. No. 5,118,801.

[51] Int. Cl.⁵ .................. C12Q 1/68; C12P 19/34
[52] U.S. Cl. ...................... 435/6; 435/91.1; 935/77; 935/78
[58] Field of Search ............ 435/6.91; 436/501, 94; 536/27; 935/77, 78

[56] References Cited

U.S. PATENT DOCUMENTS

| | | | |
|---|---|---|---|
| 4,551,433 | 11/1985 | DeBoer | 435/6 |
| 4,683,202 | 7/1987 | Mullis | 435/6 |
| 4,710,464 | 12/1987 | Belagaje et al. | 435/91 |
| 4,725,537 | 2/1988 | Fritsch et al. | 536/28 |

FOREIGN PATENT DOCUMENTS

| | | |
|---|---|---|
| 57754 | 11/1986 | Australia . |
| 68341 | 7/1987 | Australia . |
| 0224126 | 6/1987 | European Pat. Off. . |
| 8706270 | 10/1987 | PCT Int'l Appl. . |

OTHER PUBLICATIONS

E. Engelke et al., "Direct sequencing of enzymatically amplified human genomic DNA", Proc. Natl. Acad. Sci. USA 85:544–548 (1988).

B. Kalisch et al., "Covalently linked sequencing primer linkers (splinkers) for sequencing analysis of restriction fragments", Gene 44:263–270 (1986).

S. Krawetz et al., "Covalently linked complementary oligodeoxynucleotides (splinkers) as tools for molecular biology," Nucleic Acids research 14:7131 (1986).

Kramer, et al., "Replicatable RNA reporters", Nature 339:401–402 (1989).

Nishihara, Tohru, et al., "Localization of the Q Replicase Recognition Site in MDV-1 RNA", J. Biochem. 93:669–674.

Chu, et al., Synthesis of an amplifiable reporter RNA for bioassays 14(14) Nuc. Acids Res. 5591–5603 (1986).

Szybalski, Universal research in endonucleases: designing novel cleavage specificities by combining adapter oligodeoxy nucleotide and enzyme moieties. 40 Gene 169–73 (1985).

Primary Examiner—Stephanie W. Zitomer
Attorney, Agent, or Firm—Davis Hoxie Faithfull & Hapgood

[57] ABSTRACT

A probe for the detection of a nucleic acid target sequence containing a molecular switch comprising three essential elements: a probe sequence of 20–60 nucleotides surrounded by switch sequences of 10–40 nucleotides which are complementary to each other, wherein the state of the switch is useful for selectively generating a detectable signal if the probe is hybridized to a target; also, assays and kits utilizing such probes.

23 Claims, 4 Drawing Sheets

ASSAYS AND KITS INCORPORATING NUCLEIC ACID PROBES CONTAINING IMPROVED MOLECULAR SWITCH

This is a divisional of copending U.S. application(s) Ser. No. 07/251,696, filed Sep. 30, 1988, now U.S. Pat. No. 5,118,801.

This invention relates to the field of bioassays that involve nucleic acid hybridization probes. These bioassays are useful for the detection of specific genes, gene segments or RNA molecules. The assays are useful clinically, for, e.g., tissue, blood and urine samples, as well as in food technology, agriculture, and biological research.

BACKGROUND OF THE INVENTION

The use of nucleic acid hybridization probes for bioassays is well known. One of the early papers in the field directed to assays for DNA is Gillespie, D. and Spiegelman, S., A Quantitative Assay for DNA-RNA Hybrids with DNA Immobilized on a Membrane, *J. Mol. Biol.* 12:829-842 (1965). In general terms such an assay involves separating the nucleic acid polymer chains in a sample, as by melting, fixing the separated DNA strands to a nitrocellulose membrane, and then introducing a probe sequence which is complementary to a unique sequence of the material being sought, the "target" material, and incubating to hybridize probe segments to complementary target segments, if targets are present. Non-hybridized probes are removed by known washing techniques, and then the amount of probe remaining is determined by one of a variety of techniques outlined below which provides a measurement of the amount of targets in the sample.

A more recently developed form of bioassay that uses nucleic acid hybridization probes involves a second probe, often called a "capture probe." Ranki, M., Palva, A., Virtanen M., Laaksonen, M., and Soderlund, H., Sandwich Hybridization as a convenient Method for the Detection of Nucleic Acids in Crude Samples, *Gene* 21:77-85 (1983); Syvanen, A.-C., Laaksonen, M., and Soderlund, H., Fast Quantification of Nucleic Acid Hybrids by Affinity-based Hybrid Collection, *Nucleic Acids Res.* 14:5037-5048 (1986). A capture probe contains a nucleic acid sequence which is complementary to the target, preferably in a region near the sequence to which the radioactively labeled probe is complementary. The capture probe is provided with a means to bind it to a solid surface. Thus, hybridization can be carried out in solution, where it occurs rapidly, and the hybrids can then be bound to a solid surface. One example of such a means is biotin. Langer, P. R., Waldrop, A. A. and Ward, D. C., Enzymatic Synthesis of Biotin-Labeled Polynucleotides: Novel Nucleic Acid Affinity Probes, *Proc. Natl. Acad. Sci. USA* 78:6633-6637 (1981). Through biotin the capture probe can be bound to streptavidin covalently linked to solid beads.

The present invention is directed to the methods and means, including assays and pharmaceutical kits containing requisite reagents and means, for detecting in an in vitro or ex vitro setting the presence of nucleic acid species.

It is a goal in this art to detect various nucleic acid sequences in a biological sample, in which the said sequences, as so-called target sequences, are present in small amounts relative to its existence amongst a wide variety of other nucleic acid species including RNA, DNA or both. Thus, it is desirable to detect the nucleic acid encoding polypeptides that may be associated with pathological diseases or conditions, such as, for example, RNA of the human immunodeficiency virus. In addition to the detection of nucleic acids encoding the proteins of such viral particles, it is desirable to detect other nucleic acids characteristic of a pathological disease or condition such as a defective gene, as in the case of hemophilia. It is also desirable to detect other nucleic acids whose presence in the sample indicates that the organism is able to resist the action of a drug, such as an antibiotic.

Several approaches have been used for detecting the probe. One is to link a readily detectable reporter group to the probe. Examples of such reporter groups are fluorescent organic molecules and $^{32}$P-labeled phosphate groups. These detection techniques have a practical limit of sensitivity of about a million targets per sample.

A second approach is to link a signal generating system to the probe. Examples are enzymes such as peroxidase. Probes are then incubated with a color-forming substrate. Leary, J. J., Brigati, D. J. and Ward, D. C., Rapid and Sensitive Colorimetric Method for Visualizing Biotin-Labeled DNA Probes Hybridized to DNA or RNA Immobilized on Nitrocellulose: Bio-Blots, *Proc. Natl. Acad. Sci. USA* 80:4045-4049 (1983). Such amplification reduces the minimum number of target molecules which can be detected. As a practical matter, however, nonspecific binding of probes has limited the improvement in sensitivity as compared to radioactive tagging to roughly an order of magnitude, i.e., to a minimum of roughly 100,000 target molecules.

Yet another approach is to make many copies of the target itself by in vivo methods. Hartley, J. L., Berninger, M., Jessee, J. A., Bloom, F. R. and Temple, G. S., Bioassay for Specific DNA Sequences Using a Non-Radioactive Probe, *Gene* 49:295-302 (1986). This can also be done in vitro using a technique called "polymerase chain reaction" (PCR). This technique was reported in Saiki, R. K., Scharf, S., Faloona, F., Mullis, K. B., Horn, G. T., Erlich, H. A., and Arnheim, N., Enzymatic Amplification of Beta-globin Genomic Sequences and Restriction Site Analysis for Diagnosis of Sickle Cell Anemia, *Science* 230:1350-1354 (1985); Saiki, R. K., Gelfand, D. H. Stoffel, S., Scharf, S. J., Higuchi, R., Horn, G. T., Mullis, K. B., and Erlich, H. A., Primer-directed Enzymatic Amplification of DNA With a Thermostable DNA Polymerase, *Science* 239:487-491 (1988); Erlich, H. A., Gelfand, D. H., and Saiki, R. K., Specific DNA Amplification, *Nature* 331:461-462 (1988), and Mullis et al., European Patent Application Publication Nos. 200362 and 201184 (see also U.S. Pat. Nos. 4,683,195 and 4,683,202). In PCR, the probe is complementary only to the beginning of a target sequence but, through an enzymatic process, serves as a primer for replication of an entire target. Each repetition of the process results in another doubling of the number of target sequences until a large number, say, a million copies, of the target are generated. At that point detectable probes, e.g., radioactively labeled probes, can be used to detect the amplified number of targets. The sensitivity of this method of target amplification is generally limited by the number of "false positive signals" generated, that is, generated segments that are not true copies of the target. Nonetheless, this method is quite sensitive. The procedure requires at least two nucleic acid probes and has three steps for a single cycle. This procedure is cumbersome and not always reliable.

Yet another method for amplification is to link to the probe an RNA that is known to be copied in an exponential fashion by an RNA-directed RNA polymerase. An example of such a polymerase is bacteriophage Q-beta replicase. Haruna, I., and Spiegelman, S., Autocatalytic Synthesis of a Viral RNA *In Vitro, Science* 150:884–886 (1965). Another example is brome mosaic virus replicase. March et al., POSITIVE STRAND RNA VIRUSES Alan R. Liss, New York (1987). In this technique, the RNA serves as a template for the exponential synthesis of RNA copies by a homologous RNA-directed RNA polymerase. The amount of RNA synthesized is much greater than the amount present initially. This amplification technique is disclosed in Chu, B. C. F., Kramer, F. R., and Orgel, L. E., Synthesis of an Amplifiable Reporter RNA for Bioassays, *Nucleic Acids Res.* 14:5591–5603 (1986); Lizardi, P. M., Guerra, C. E., Lomeli, H., Tussie-Luna, I. and Kramer, F. R., Exponential Amplification of Recombinant-RNA Hybridization Probes, *Bio/Technology* 6:1197–1203 (October, 1988), which is incorporated herein by reference and is attached hereto in manuscript form [hereinafter referred to as "Lizardi et al."]; published European Patent Application 266,399 (EP Application No. 87903131.8). After non-hybridized probes are removed by washing, the RNA polymerase is used to make copies of the replicatable RNA. According to the disclosure of published European Patent Application No. 266,399, replication of the RNA may take place while the RNA is linked to the probe. Alternatively, the replicatable RNA may be separated from the remainder of the probe prior to replication. That application also discloses a variety of chemical links by which a probe sequence can be joined to a replicatable RNA. In addition, it discloses that the probe sequence may be part of a replicatable RNA, as described in Miele, E. A., Mills, D. R., and Kramer, F. R., Autocatalytic Replication of a Recombinant RNA, *J. Mol. Biol.* 171:281–295 (1983). That European application also discloses that such recombinant RNAs must be able to hybridize specifically with the target sequence as well as to retain their ability to serve as a template for exponential replication by an appropriate RNA-directed RNA polymerase, as is demonstrated in the results obtained by Lizardi et al., supra.

Replication of RNA, as opposed to target amplification using PCR, can be done in a single step. In that step one can synthesize as many as a billion copies of the replicatable RNA that was joined to the probe in as little as twenty minutes, which theoretically could lead to detection of a single target molecule. However, in practice the sensitivity of this type of probe replication is limited by the persistence of nonspecifically bound probes. Nonspecifically bound probes will lead to replication just as will probes hybridized to targets.

A major problem in the implementation of bioassays that employ hybridization technology coupled to signal amplification systems is the background signal produced by nonspecifically bound probe molecules. These background signals introduce an artificial limit on the sensitivity of bioassays. In conventional bioassays this problem is sometimes alleviated by the utilization of elaborate washing schemes that are designed to remove nonspecifically bound probes. These washing schemes inevitably add to the complexity and cost of the assay.

As a means to reduce the background noise level of assays employing probes linked to replicatable RNA by covalently joined linking moieties, European Patent Application No. 266,399 discloses what it refers to as "smart probes," that is, probes whose linked RNA is said not to serve as a template for replication unless and until the probe has hybridized with a target sequence. In that application two embodiments are disclosed for smart probes.

In a first embodiment in that application, the smart probe comprises a probe portion consisting of about 75–150 deoxynucleotides, made by in vitro or in vivo methods known in the art. The smart probe also comprises a recombinant, replicatable RNA containing an inserted heterologous sequence of about 10–30 nucleotides, made by, e.g., the method of Miele, E. A., Mills, D. R., and Kramer, F. R., Autocatalytic Replication of a Recombinant RNA. *J. Mol. Biol.* 171:281–295 (1983). Joining those two portions at their 5' ends is a linking moiety of the formula —O(PO$_2$)NH(CH$_2$)$_a$SS(CH$_2$)$_b$NH(PO$_2$)O—, where a and b are each 2 to 20. Furthermore, the sequence at the 3' end of the DNA portion of the smart probe is capable of being (and very likely to be) hybridized to the heterologous sequence of the RNA portion of the smart probe. The enzyme ribonuclease H is said to be capable of cleaving the RNA portion of smart probes which have not hybridized to targets, but not be capable of cleaving the RNA portion of smart probes which have hybridized to targets, because when the probe sequence in the DNA portion of a smart probe is bound to its target, it is said to be incapable of also being hybridized to the heterologous sequence in the RNA portion of the smart probe, thereby providing a way to eliminate nonspecifically bound probes prior to amplification. Amplification via RNA replication is said to optionally include the preliminary step of cleaving the disulfide bond in the linking moiety.

In that embodiment, cleavage of probes not hybridized to targets is said to be possible for ribonuclease H, because the 3' end of the DNA portion of the smart probe (which contains the probe sequence) is hybridized to the recombinant replicatable RNA portion, presumably thereby providing a site wherein ribonuclease H can cleave the RNA and render it inoperative as a template for amplification by an RNA-directed RNA polymerase.

In the other embodiment of a smart probe disclosed in published European Patent Application 266,399, there is a probe portion, a linking moiety, and a replicatable RNA portion, linked as described above. Here, however, the probe portion comprises not only a probe segment of 50–150 nucleotides, but also additional segments, called "clamp" segments, on either side of it, that is, a 5'-clamp segment and a 3'-clamp segment, each of about 30–60 nucleotides. Each clamp segment is said to hybridize with a segment of the replicatable RNA portion, rendering the RNA inactive as a template for replication, unless and until the probe is hybridized with a target. That hybridization causes the clamps to release, thereby rendering the RNA replicatable, either directly or after optional cleavage of the disulfide bond.

The smart probes disclosed in published European Patent Application No. 266,399 comprise a somewhat complicated linking moiety containing a weakly covalent and rather easily dissociable disulfide linkage. Disulfide bonds readily dissociate under reducing conditions. The two versions of smart probes disclosed in that application rely on distant intramolecular interactions to render the probe smart. This is a disadvantage which makes such probes difficult to design, particularly since distant interactions are not well understood. The second version, reported above, has a further complication that it utilizes two distant clamps which must displace a set of relatively strong neighboring compliments. And, the design depends on both distant clamps hybridizing or none, which makes design very difficult.

An object of the present invention is a simple molecular allosteric switch that renders a nucleic acid hybridization probe smart, that is, capable, in an appropriate assay, of generating a signal only if the probe is hybridized to a target sequence.

It is a further object of this invention to couple the activity of a signal generating system to the state of such a switch.

It is yet another object of this invention to develop probes containing such an allosteric switch that are linked to any of a number of different signal generating systems whose activity is dependent on the state of the switch.

It is another object of this invention to develop assays of improved sensitivity that utilize the above constructs, as well as kits for performing such assays.

SUMMARY OF THE INVENTION

The present invention is predicated on a simple molecular allosteric switch that works on the principle that when a nucleic acid double helix is formed between a relatively short probe sequence and a target sequence, the ends of the double helix are necessarily located at a distance from each other due to the rigidity of the double helix. That rigidity is discussed in detail in Shore, D., Langowski, J. and Baldwin, R. L., DNA Flexibility Studied by Covalent Closure of Short Fragments into Circles, *Proc. Natl. Sci. USA* 78:4833–4837 (1981); and Ulanovsky, L., Bodner, M., Trifonov, E. N., and Choder, M., Curved DNA: Design, Synthesis, and Circularization, *Proc. Natl. Acad. Sci. USA* 83:862–866 (1986).

This invention involves the use of a nucleic acid hybridization probe comprising at least the following essentials: a probe sequence of approximately 15–115 nucleotides in length surrounded on both sides by complementary nucleic acid sequences which are considerably shorter than the probe sequence, preferably not greatly in excess of one-half the length of the probe sequence. This combination of three sequences forms a simple molecular allosteric switch. When not hybridized to a target sequence, the switch sequences are hybridized to each other, which we refer to as a closed switch. When the probe sequence hybridizes to a predetermined complementary target sequence for which the probe is designed, the strong interaction between the probe and target sequences to form a rigid double helix necessarily results in the dissociation of the switch sequences, which we refer to as an open switch. In the open configuration, the switch sequences are unable to interact with each other.

The invention comprises probe molecules containing the above switch wherein one of the switch sequences, or both switch sequences in combination, comprise a biologically functional nucleic acid moiety useful for selectively generating a detectable signal indicative of the hybridization of the probe with its predetermined target sequence.

The invention further comprises bioassay methods which take advantage of the allosteric change in the switch sequences in the above probe molecules to generate a detectable signal indicative of the hybridization of the probe with its predetermined target sequence. The assay may be qualitative (a qualitative demonstration) or quantitative (a quantitative determination). It may include amplification, which may be linear or exponential in nature.

The invention also includes kits of reagents and macromolecules for carrying out the above bioassays.

DETAILED DESCRIPTION OF THE INVENTION

Figure 1:
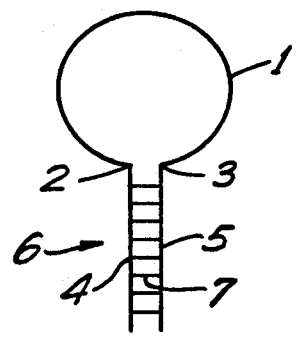
FIG. 1 is a schematic representation of a closed switch according to the invention.
Figure 2:
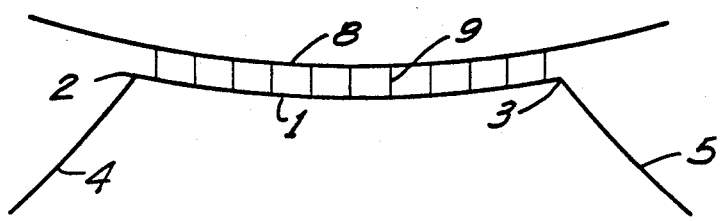
FIG. 2 is a schematic representation of the switch of FIG. 1, but in an open state.

Shown in FIG. 1 is a probe, or probe portion, comprising the three essential ingredients of a probe according to this invention, namely, a probe sequence and complementary switch sequences on both sides of the probe. As depicted in FIG. 1, the switch is closed. FIG. 2 is the same probe or probe portion in its open state.

Referring to FIG. 1, probe sequence 1 is a nucleic acid probe sequence extending from its 5' side 2 to its 3' side 3. Immediately adjacent to the 5' side of the probe sequence is a nucleic acid first switch sequence 4. Immediately adjacent to the 3' side of the probe sequence is a nucleic acid second switch sequence 5. Switch sequences 4 and 5 are complementary and hybridize to each other via hydrogen bonds 7, forming the stem 6 of a "hairpin" secondary structure. Referring to FIG. 2, probe sequence 1 is hybridized via hydrogen bonds 9 to its predetermined target sequence 8. Switch sequences 4 and 5 are apart and not interacting with one another.

The probe may be RNA or DNA. The probe sequence 1 must be of sufficient length to ensure a very specific interaction with its predetermined target sequence 8. It should be at least about 15 nucleotides in length, although we prefer that it be at least about 20 nucleotides in length.

The probe sequence 1 should be short enough to ensure that the sides 2, 3 of probe sequence 1, when hybridized to the target sequence 8 (FIG. 2) are physically prevented by the rigidity of the hybridized region between sides 2 and 3 from approaching each other within a distance that would permit switch sequences 4, 5 from interacting with each other. In other words, when the probe sequence is hybridized, the switch sequences necessarily are not hybridized to each other. An additional force helps to drive the transition to an open state, namely, torsional forces tending to unwind stem 6 when the hybridized region shown in FIG. 2 forms a double helix. In practice, the probe sequence is no longer than about 100 nucleotides. We prefer that the probe sequence be 20–60 nucleotides in length, and most preferably, about 30 nucleotides in length.

The switch sequences are related to the length of the probe sequence. Most preferably, we prefer that the length of the switch sequences be no more than half the length of the probe sequence. The switch sequences should be at least about 10 nucleotides in length to permit formation of a stable stem 6. Turner, D. H., Sugimoto, N., Jaeger, J. A., Longfellow, C. E., Freier, S. M. and Kierzek, R., Improved Parameters for Prediction of RNA Structure, *Cold Spring Harbor Symp. Quant. Biol.* 52:123-133 (1987). The length of switch sequences for certain embodiments described below must also be sufficiently long to contain necessary functional sequences. We prefer switch sequences of about 10–40 nucleotides or preferably about 10–30 nucleotides.

In designing a probe according to the invention, attention should be paid to the relative strengths of the open switch hybrid (FIG. 2) as compared to the closed switch hybrid (FIG. 1) under the assay conditions to be used: the former should be greater. There are assay conditions, however, in which the strengths of hybrids is only length-dependent. Wood, W. I., Gitschier, J., Lasky, L. A., and Lawn, R. M., Base Composition-independent Hybridization in Tetramethylammonium Chloride: A Method for oligonucleotide Screening of Highly Complex Gene Libraries, *Proc. Natl. Acad. Sci. USA* 82:1585–1588 (1985).

Switch design can be readily tested by digesting probes or probe portions (FIGS. 1, 2) with appropriate nucleases before and after hybridization to model nucleic acids containing target sequences and then analyzing the digestion products by polyacrylamide gel electrophoresis. This will be apparent to those skilled in the art and will not be described further.

To help drive the transition from closed to open, one may take advantage of the principle of strand displacement to provide an additional force. Green, C., and Tibbetts, C., Reassociation Rate Limited Displacement of DNA Strands by Branch Migration, *Nucleic Acids Res.* 9:1905–1918 (1981). This may be accomplished by overlapping a switch sequence with a probe sequence, which means that at least one nucleotide of the switch sequence is also a nucleotide of the probe sequence.

While the switch sequences must be adjacent to the probe sequence, they need not be immediately adjacent to it. A few nucleotides may separate the switch sequences from the probe sequences, but not so many that the functioning of the switch is materially affected, as those skilled in the art will readily appreciate.

Probe molecules of this invention, containing the switch described above, can be of diverse design and still take advantage of the allosteric change that accompanies probe sequence hybridization (FIG. 2) in signal generation.

For example, a switch sequence may, by virtue of the conformation it assumes in the open state, enable an interaction with another macromolecule, or even a different portion of the same molecule, which is required for the generation of a detectable signal. In Example I below, the second switch sequence, in the open state, is able to hybridize with a complementary nucleic acid strand. In Example III, the first switch sequence, in the open state, forms a hairpin structure that enables it to bind specifically to a viral protein. In Example IV, the second switch sequence, in the open state, is able to interact with an oligoribonucleotide or with an oligodeoxyribonucleotide. In Example V, the first switch sequence, in the open state, assumes a structured conformation that enables it to interact with a relatively distant region of the same probe molecule.

It is also possible to do the reverse. In Example II, the switch sequences can bind to a specific enzyme only when they are in the closed state.

Signal generation using probe molecules and methods of this invention may vary widely. The state of the simple allosteric switch governs signal generation, which means that there is no signal generated unless the probe sequence hybridizes with its target sequence. We prefer signal generating systems that involve amplification, particularly exponential amplification, to increase sensitivity.

The Examples which follow illustrate a few of the myriad variations involving amplification. They all utilize the exponential replication of a replicatable RNA by an RNA-directed RNA polymerase to generate a readily detectable signal. The Examples utilize MDV-1 RNA, which is described in Kacian, D. L., Mills, P. R., Kramer, F. R., and Spiegelman, S., A Replicating RNA Molecule Suitable for a Detailed Analysis of Extracellular Evolution and Replication, *Proc. Nat. Acad. Sci. USA* 69:3038–3042 (1972). The Examples also use Q-beta replicase, which is the specific polymerase for replicating MDV-1 RNA. Q-beta replicase is described in Haruna, I. and Spiegelman, S., Specific Template Requirements of RNA Replicases, *Proc. Nat. Acad. Sci. USA* 54:579–587 (1965). Any replicatable RNA and its homologous replicase could, of course, be used. Other useful signal generating systems could employ enzymes, enzyme cofactors, ribozymes, DNA and RNA sequences required for biological activity (e.g., promoters, primers, or linkers required for the ligation of plasmids used to transform bacteria). Detectable signals are diverse and include, for example, radiation, light absorption, fluorescence, mass increase, and the presence of biologically active compounds.

Assay techniques which can be used to detect hybridized probes of this invention are also diverse. In the following Examples, synthesis of a replicatable RNA is used to signal that hybridization of the probe sequence has occurred. The signal generating systems illustrated in the Examples fall into three broad classes: in Examples II–III, the switch is incorporated within a replicatable RNA; in Examples IV–V, a replicatable RNA sequence is joined with a probe portion but can only be replicated after cleavage, which is dependent upon the presence of an open switch; and in Example I, the transcription of a replicatable RNA from a template added after hybridization, can only occur when an open switch sequence forms a part of a functional promoter of transcription.

Each of the specific embodiments set forth in the accompanying Examples satisfies the objective of generating a signal only if the probe is hybridized to a target sequence. Either the biological activity of the signal generating systems illustrated depends strictly on the state of the switch, or the state of the switch provides a means for rendering nonspecifically bound probes unable to generate signals, or the state of the switch provides a means for separating hybridized probes from nonspecifically bound probes. Thus, each of the specific embodiments markedly reduces the background caused by nonspecifically bound probes, thereby significantly improving the sensitivity of the assays, including assays which include amplification.

EXAMPLE I

In this example, the probe is a single DNA strand designed to contain three sequences: a probe sequence approximately 34 nucleotides in length; a first switch sequence of about 17 nucleotides immediately adjacent to the 5' side of the probe sequence; and a second switch sequence of about 17 nucleotides immediately adjacent to the 3' side of the probe sequence. The switch sequences are designed to be complementary to one another. When hybridized to each other, the hybridized switch sequences comprise a promoter for the DNA-directed RNA polymerase, bacteriophage T7 RNA polymerase. In this application, we refer to the first switch sequence as a "promoter sequence" and the second switch sequence as a "promoter-complement" sequence. In this example, the switch sequences comprise the ends of the probe molecule. The design of promoter and promoter-complement sequences is according to Osterman, H. L. and Coleman, J. E., "T7 Ribonucleic Acid Polymerase-Promoter Interactions," *Biochemistry* 20:4885-4892 (1981). The particular promoter-complement sequence we have chosen to work with is TAATACGACTCACTATA.

The probe molecule, including a probe sequence complementary to a predetermined target sequence, can be made by chemical synthesis of oligodeoxyribonucleotides using methods well known in the art, e.g., Gait, M. J., OLIGONUCLEOTIDE SYNTHESIS, IRL Press, Oxford, United Kingdom (1984).

The probe of this example can be used to detect a DNA or RNA target sequence which is complementary to the probe sequence. The target sequence may be in a sample containing other, unrelated nucleic acids and other materials, for example, proteins. The probe may be used to detect a gene segment of an infectious agent (virus, bacterium, protozoan, etc.) in a clinical sample of, for example, human blood or urine.

The target sequence must be exposed to the probe. This is done by techniques well known to the art. Commonly, but not necessarily, nucleic acid is isolated from a sample before the probe is added.

The probe and the sample, which may contain nucleic acid target sequences, are next incubated under conditions, including time and temperature, appropriate to cause hybridization of probe sequences with target sequences. Appropriate conditions are well known in the art. For quantitative determination of the number of target sequences present, an amount of probe in excess, preferably in substantial excess, of the highest anticipated target amount should be used. If only a qualitative demonstration of the presence of target sequences is desired, a lesser amount of probe can be used.

Probes hybridized to targets are separated from unbound probes by methods well known to the art, for example, through the use of capture probes.

After separation, the treated sample will contain probes hybridized to targets (FIG. 2) and also non-specifically bound probes. The two are not in the same form, however. In the hybridized probes the allosteric switches are open; that is, the switch sequences are not hybridized to each other. In the nonspecifically bound probes, however, the switch sequences remain hybridized to each other.

Detecting those probes with open switches will now be described. This example includes amplification prior to detection.

Figure 3:
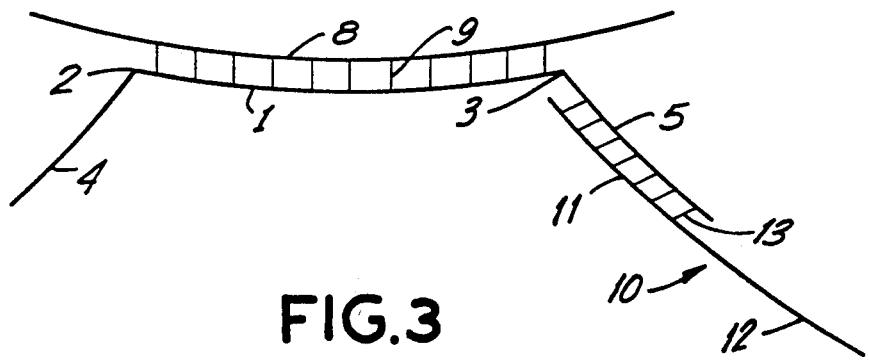
FIG. 3 is a schematic representation of the probe of Example I, containing a switch in an open state.

Referring to FIG. 3, the sample is incubated with a single-stranded DNA molecule 10 comprising a promoter sequence 11 and a template sequence 12 for the transcription of a replicatable RNA. The promoter sequence 11 allows hybridization via hydrogen bonds 13, under conditions known to the art, to the promoter-complement of the second switch sequence 5 of probes having open switches. Specifically, this DNA molecule consists of the 17 deoxyribonucleotides of the promoter sequence (complementary to the promoter-complement set forth above) followed by the 244 deoxyribonucleotides complementary to MDV-poly (+) RNA described in Lizardi et al., supra. This DNA molecule can be prepared by isolating one of the complementary strands of a suitable restriction fragment of a plasmid containing that sequence by methods known in the art. Maniatis, T., Fritsch, E. F., and Sanbrook, J., MOLECULAR CLONING: A LABORATORY MANUAL Cold Spring Harbor Laboratory, Cold Spring Harbor, N.Y. (1982). The suitable plasmid that we constructed contained (1) a unique restriction site (that is, one contained nowhere else in the plasmid) upstream from and close to the promoter, and (2) and Sma I restriction site at the end of the MDV-Poly CDNA sequence distal to the promoter.

Subsequently, the sample is incubated with commercially available cloned bacteriophage T7 RNA polymerase in order to synthesize about 50-200, or more, MDV-poly RNA transcripts for each open switch, using conditions known to the art. Milligan, J. F., Duncan, R. G., Witherell, G. W. and Uhlenbeck, O. C., Oligoribonucleotide Synthesis Using T7 RNA Polymerase and Synthetic DNA Templates, *Nucleic Acids Research* 15:8783-8798 (1987).

Then, Q-beta replicase, an RNA-directed RNA polymerase, is added and incubated with the MDV-poly RNA transcripts, which are templates for that polymerase. We prepared Q-beta replicase by the method of Eoyang, L., and August, J. T., Q-beta RNA polymerase from phage Q-beta-infected *E. coli*, pp. 829-839. *In: Procedures in Nucleic Acid Research*, Volume 2. (Cantoni, G. L., and Davis, D. R., eds.). Harper and Row, New York (1971). Incubation is carried out under conditions suitable for exponential amplification of the transcripts. Kramer, F. R., Mills, D. R., Cole, P. E., Nishihara, T., and Spiegelman, S., Evolution in vitro: Sequence and Phenotype of a Mutant RNA Resistant to Ethidium Bromide. *J. Mol. Biol.* 89:719-736 (1974).

Detection of the exponentially amplified RNA can be done by any of a variety of physical and chemical means, as described earlier in this application. For a quantitative determination, the amount of RNA detected after a fixed time of incubation with the RNA-directed RNA polymerase is a measure of the number of target sequence present in the sample.

EXAMPLE II

Figure 4:
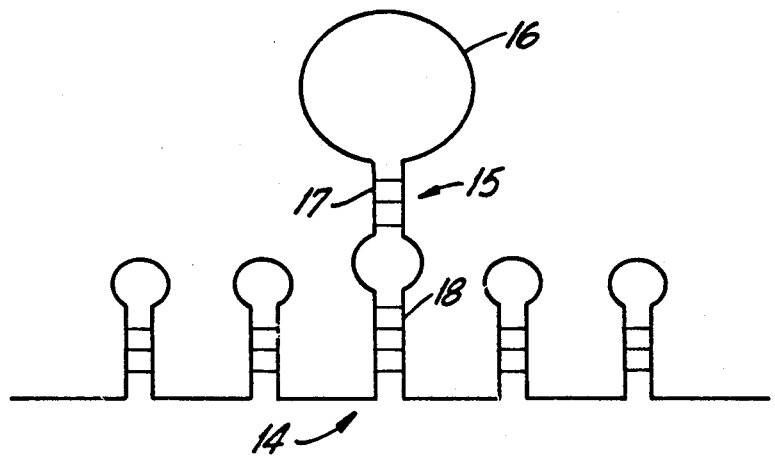
FIG. 4 is a schematic representation of the probe of Example II, containing a switch in an closed state.

Referring to FIG. 4, in this example, the probe is a replicatable recombinant RNA 14. Miele, E. A., Mills, D. R., and Kramer, F. R., Autocatalytic Replication of a Recombinant RNA, *J. Mol. Biol.* 171:281-295 (1983). It may be prepared according to the method of Lizardi et al., supra. For purposes of preparing a probe according to this example, the heterologous sequence 15 contained within the replicatable recombinant RNA is designed to contain three sequences: a probe sequence 16 approximately 46 nucleotides in length; a first switch sequence 17 of about 23 nucleotides immediately adjacent to the 5' side of the probe sequence; and a second switch sequence 18 of about 23 nucleotides immediately adjacent to the 3' side of the probe sequence. The switch sequences are designed to form a double-stranded recognition site for *Escherichia coli* ribonuclease III when hybridized to each other. This recognition site will not be present when the switch sequences are not hybridized to each other. The particular recognition site we use is shown in FIG. 4 and is described by Rosenberg, M. and Kramer, R. A., Nucleotide Sequence Surrounding a Ribonuclease III Processing Site in Bacteriophage T7 RNA, *Proc. Natl. Acad. Sci. USA* 74:984-988 (1977). It can be made by transcription from a recombinant plasmid utilizing techniques described in Lizardi et al., supra.

Figure 5:
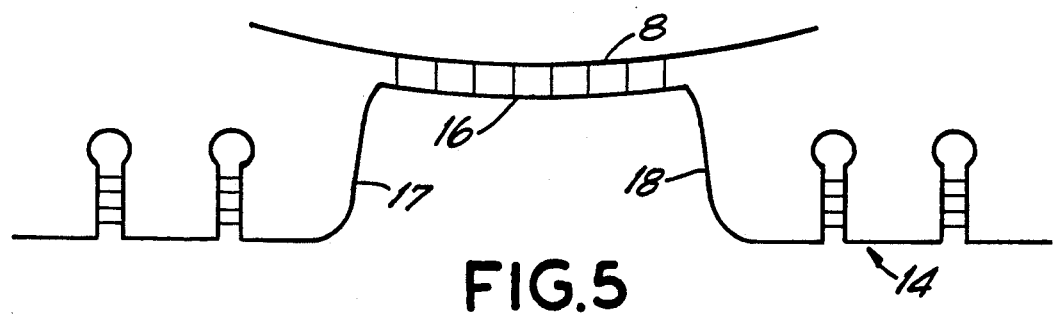
FIG. 5 is a schematic representation of the probe of Example II, containing a switch in an open state.

Exposure of the target sequence, hybridization of the probe with the target sequence, and separation from unbound probes, are as described in Example I. As shown in FIG. 5, probe sequence 16 of a hybridized probe 14 is hybridized to target sequence 8, thereby forcing apart switch sequences 17, 18.

The sample is then incubated with *E. coli* ribonuclease III under appropriate conditions known to the art to cleave all the nonspecifically bound probes (and any unbound probes which may remain), rendering them unable to serve as templates for exponential replication by Q-beta replicase. Nishihara, T., Mills, D. R., and Kramer, F. R., Localization of the Q-beta Replicape Recognition Site in MDV-1 RNA, *J. Biochem.* 93:669-674 (1983). The ribonuclease III is then removed from the sample by methods, e.g., phenol extraction, well known in the art.

We release the probe from the target sequence by a brief heating step, Lizardi et al. supra, although preliminary experiments have indicated that this step may be optional.

Exponential replication of the probe by Q-beta replicase and detection proceed as described in Example I.

EXAMPLE III

Figure 6:
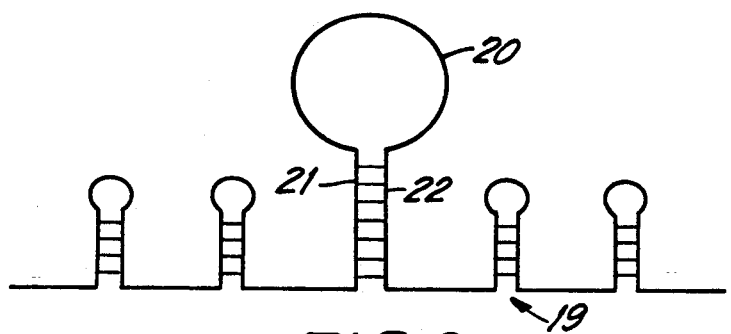
FIG. 6 is a schematic representation of the probe of Example III, containing a switch in an closed state.
Figure 7:
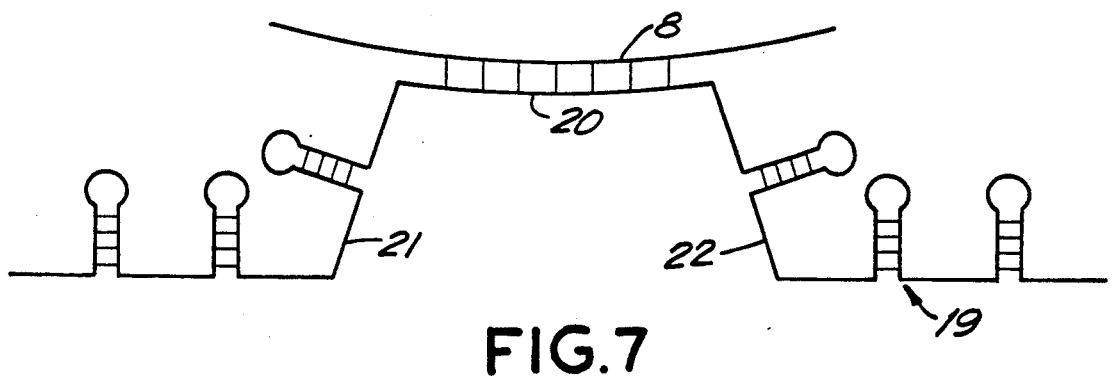
FIG. 7 is a schematic representation of the probe of Example III, containing a switch in an open state.

In this example the probe 19 (FIG. 6) is a replicatable recombinant RNA as in Example II, except that the probe sequence 20 is about 38 nucleotides in length and that the complementary switch sequences 21, 22, of about 19 nucleotides, are designed such that when they are hybridized to one another they do not form a binding site for the coat protein of bacteriophage R17, but when not so hybridized, as shown in FIG. 7, the first switch sequence 21 organizes so as to comprise a secondary structure which is a strong binding site for that coat protein. Carey, J., Cameron, V., de Haseth, P. L. and Uhlenbeck, O. C., Sequence-Specific Interaction of R17 Coat Protein With Its Ribonucleic Acid Binding Site, *Biochemistry* 22:2601-2610 (1983).

Exposure of the target sequence, hybridization of the probe with the target sequence, and separation from unbound probes are as described in Example I.

The bacteriophage R17 coat protein is covalently linked to a solid support, such as, for example, Sephadex or Sepharoic beads, magnetic beads, or microtiter plates, by methods well known in the art. An example of such a method of linkage is described in Alagon, A. J., and King, T. P., Activation of Polysaccharides with 2-Iminothiolane and Its Uses, *Biochemistry* 19:4331-4345 (1980). The washed sample, containing probes bound to target sequences and nonspecifically bound probes, is added to the insolubilized R17 coat protein. Nonspecifically bound probes are removed by washing.

We release the probe from both the R17 coat protein and the target sequence by a brief heating step, and remove the solid support.

Exponential replication of the probe by Q-beta replicase and detection proceed as described in Example I.

EXAMPLE IV

In this example, the probe 23 (FIG. 8) is a single strand of RNA designed to contain four functionally distinct sequences: a probe sequence 24 approximately 34 nucleotides in length; a first switch sequence 25 of about 17 nucleotides immediately adjacent to the 5' side of the probe sequence; a second switch sequence 26 complementary to, and of the same length as, the first and located immediately adjacent to the 3' side of the probe sequence; and a replicatable RNA sequence 27 extending from the 3' side of the second switch sequence, wherein at least five nucleotides of said replicatable RNA sequence are also nucleotides of the 3' side of the second switch sequence; that is, the replicatable RNA sequence can be considered to overlap the second switch sequence.

Figure 9:
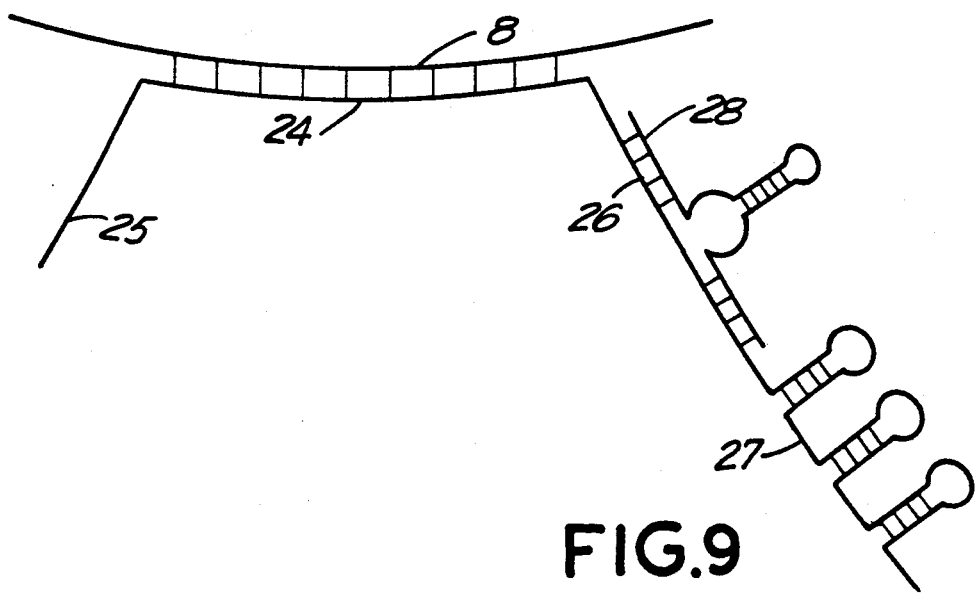
FIG. 9 is a schematic representation of the probe of Example IV, containing a switch in an open state and additionally showing a ribozyme.

Exposure of the target sequence, hybridization of probes to target sequences and separation of unbound probes are performed under appropriate conditions known to the art, as in Example I. As shown in FIG. 9, probe sequence 24 is hybridized to target sequence 8, and switch sequences 25, 26 are forced apart, thereby freeing replicatable RNA sequence 27. The replicatable RNA sequences of bound probes are, at this point, not subject to exponential replication by RNA polymerase even though the switches are open. The replicatable RNA sequences 27 must be cleaved at their 5' sides to render them subject to exponential replication. Nishihara, T., Mills, D. R., and Kramer, F. R., Localization of the Q-beta Replicase Recognition Site in MDV-1 RNA, *J. Biochem.* 93:669-674 (1983).

There are two means, at least, to cleave the replicatable RNA sequences. One is ribozyme cleavage. Another is cleavage by ribonuclease H. We prefer the former, which will be described first.

A. Ribozyme Cleavage

Ribozymes are structured RNA molecules that are capable of catalyzing a chemical reaction, such as particularly the cleavage of a phosphodiester bond. It is well known in the art that a ribozyme can be constructed by the interaction of two separate oligribonucleotides, one of which is cleaved at a particular phosphodiester bond when incubated under known, appropriate conditions. Uhlenbeck, O. C., A Small Catalytic Oligoribonucleotide, *Nature* 328:590-600 (1987); Haseloff, J. and Gerlach, W. L., Simple RNA Enzymes with New and Highly Specific Endoribonuclease Activities, *Nature* 334:585-591 (1988).

Figure 8:
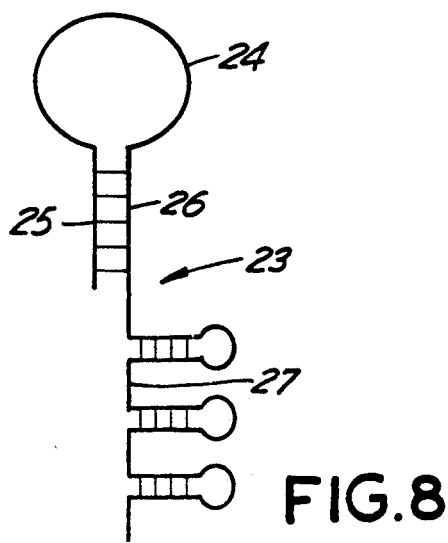
FIG. 8 is a schematic representation of the probe of Example IV, containing a switch in an closed state.

The requirements for the two segments of an active ribozyme are outlined in the two references cited above. For purposes of this invention, the second switch sequence of our probe is designed to satisfy the requirements of the sequence that is cleaved. The replicatable RNA sequence with which we have chosen to proceed is MDV-poly (+) RNA according to Lizardi et al. supra. Our preferred design is shown in FIG. 8. As shown there, the second switch sequence is 17 nucleotides in length, and 11 nucleotides of the 5' side of the MDV-poly (+) RNA are also nucleotides of the 3' side of the second switch sequence. The second switch sequence includes the required GUC sequence needed for cleavage of the phosphodiester bond on the 3' side of the GUC sequence, that is, on the 5' side of the replicatable RNA sequence. In designing the second switch sequence, care is taken to ensure that the subsequent hybridization to form the ribozyme will be more likely to occur than the interaction that can occur between the sides of the replicatable RNA sequence.

The probe can be made by transcription from a suitable recombinant plasmid. Such a plasmid is designed utilizing methods known to the art with the criteria of Lizardi et al., supra. It is constructed by methods well known to the art. Maniatis, T., Fritsch, E. F., and Sambrook, J., MOLECULAR CLONING: A LABORATORY MANUAL, Cold Spring Harbor Laboratory, Cold Spring Harbor, N.Y. (1982).

Figure 10:
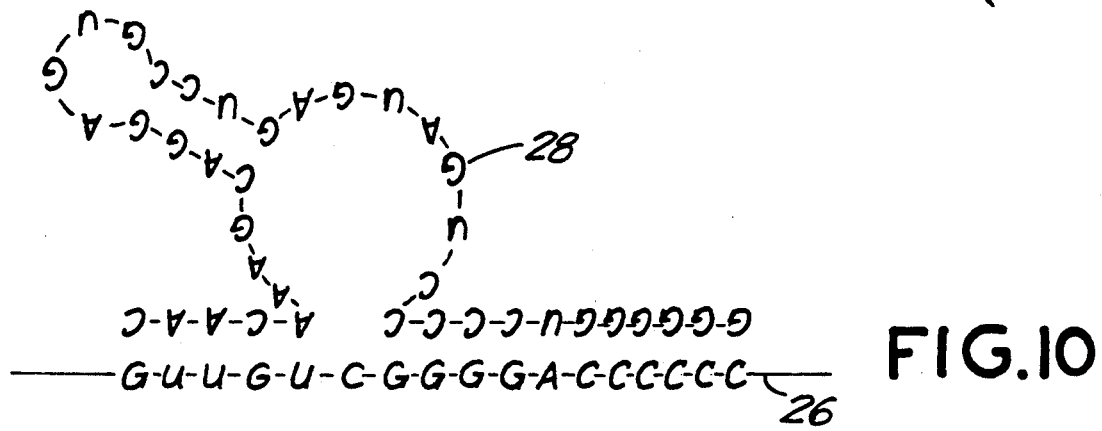
FIG. 10 is a detailed schematic showing the nucleotide sequences of the ribozyme shown in FIG. 9.

The non-cleaved strand 28, which is capable of forming the required ribozyme, is also shown in FIG. 9. It is made by methods well known to the art. Milligan, J. F., Duncan, R. G., Witherell, G. W. and Uhlenbeck, O. C., Oligoribonucleotide Synthesis Using T7 RNA Polymerase and Synthetic DNA Templates, *Nucleic Acids Research* 15:8783–8798 (1987). FIG. 10 shows the nucleotide sequences of the ribozyme formed by switch sequence 26 and strand 28 of FIG. 9.

Following separation of unbound probes, which we prefer, the non-cleaved strand 28 described above is incubated with the sample under conditions, known to the art, that will promote hybridization of that strand with the second switch sequence in probes hybridized to target sequences to form the desired ribozyme. Incubation under known conditions referred to above cleaves the replicatable RNA from those probes and permits replicatable RNA to serve as a template for exponential replication by Q-beta replicase. Referring to FIG. 10, cleavage occurs in strand 26 between the sixth and seventh nucleotides from the left as shown in the figure. Exponential replication and detection proceed as described in Example I.

B. Ribonuclease H Cleavage

The probe for this embodiment may be identical to the probe shown in FIG. 8 and described above. In this embodiment we use commercially available *E. coli* ribonuclease H, which cleaves an RNA strand when it is hybridized to a short DNA oligonucleotide within the hybridized region. Donis-Keller, H., Site Specific Enzymatic Cleavage of RNA, *Nucleic Acids Res.* 7:179–192 (1979).

Figure 11:
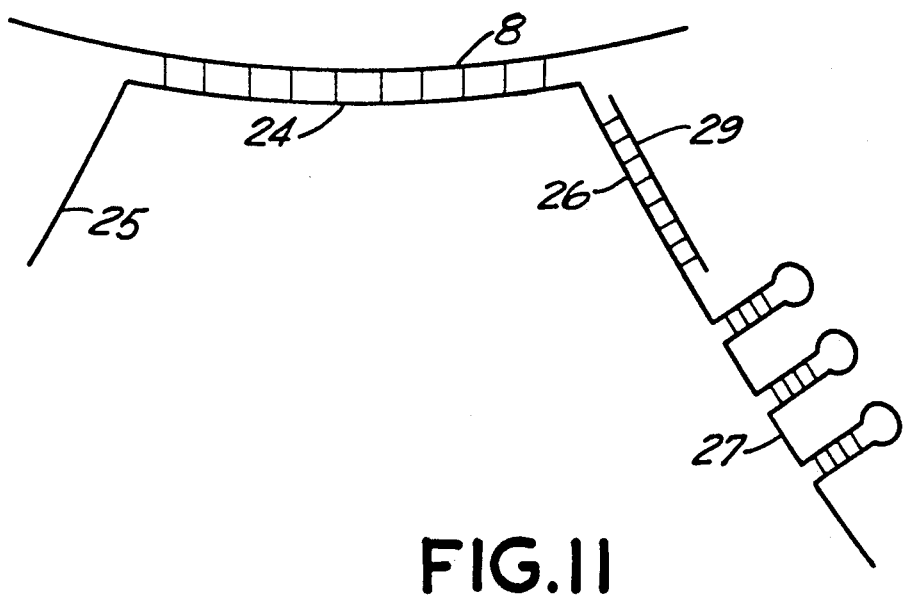
FIG. 11 is a schematic representation of the probe of Example IV, containing a switch in an open state and additionally showing an additional strand.

To take advantage of this, we synthesize a short DNA oligonucleotide 29 (FIG. 11) of about 12 nucleotides that will hybridize to the second switch sequence on both sides of the GUC sequence.

Following separation of unbound probes, which we prefer, the short DNA oligonucleotide 29 is incubated with the sample under well known conditions that will promote its hybridization (FIG. 11) to the second switch sequence. Then the ribonuclease H is added to catalyze cleavage during an incubation under known conditions. (Donis-Keller, supra). Exponential replication by Q-beta replicase and detection proceed as described in Example I.

EXAMPLE V

Figure 12:
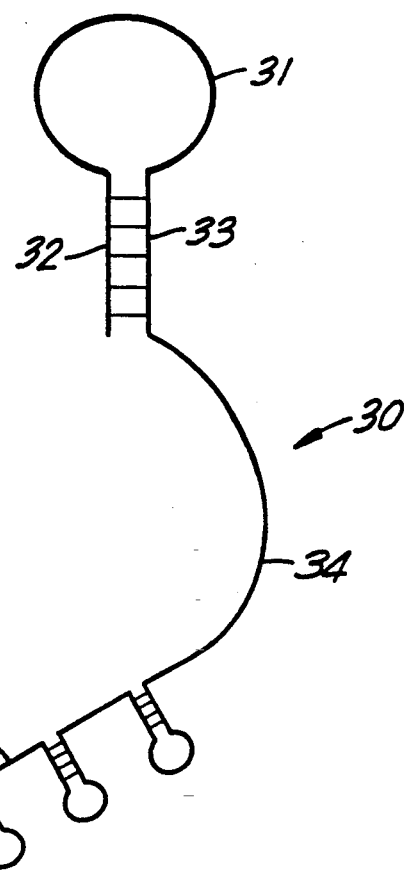
FIG. 12 is a schematic representation of the probe of Example V, containing a switch in an closed state.

This example resembles Example IV-A except that the ribozyme sequences are both part of the probe. The probe 30 (FIG. 12) is a single-stranded RNA, prepared as described in Example IV but designed to contain five sequences: a probe sequence 31 approximately 34 nucleotides in length; a first switch sequence 32 of about 17 nucleotides having the sequence of the non-cleaved strand 28 shown in FIG. 9; a second switch sequence 33 of about 17 nucleotides complementary to the first sequence, as in Example I; a spacer sequence 34 of approximately 45 nucleotides extending from the 3' side of the second switch sequence, and a replicatable RNA moiety 35. The six nucleotides at the 3' side of the spacer sequence are identical to the six nucleotides at the 5' side of the second switch sequence shown in FIG. 9. Thus, the region in which the spacer sequence is joined to the replicatable RNA sequence comprises the cleavable strand of a ribozyme, just as does the second switch sequence 26 in Example IV-A. In the unbound probe, the first switch sequence 32 is hybridized to the second switch sequence 33. In probes hybridized to target sequences, where the switch is open, however, the first switch sequence 32 is available to hybridize with the region in which the 3' side of the spacer sequence 34 is joined to the 5' side of the replicatable RNA sequence 35, thereby forming a ribozyme. The spacer 34 is designed to be long enough to permit that hybridization.

Figure 13:
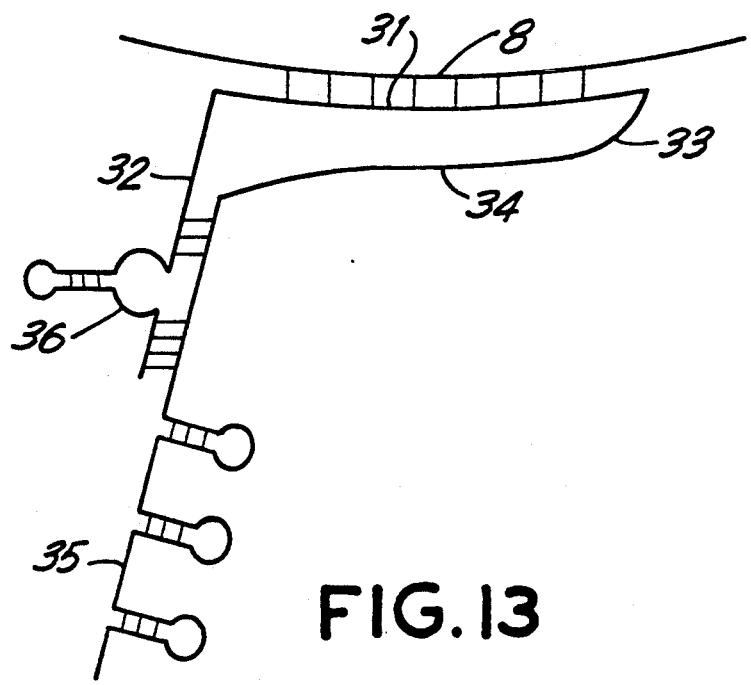
FIG. 13 is a schematic representation of the probe of Example V, containing a switch in an open state.

Exposure of the target sequence, hybridizing of probes to target sequences, and separation of unbound probes, which we prefer, is as described in Example I. Upon hybridization of a probe to a target sequence (FIG. 13), the switch sequences 32, 33 are not hybridized to each other and the ribozyme 36 is formed.

Release of the replicatable RNA, exponential replication and detection proceed as in Example IV-A.

As stated above the assays of this invention may be qualitative or quantitative. As one skilled in the art will readily appreciate, for a qualitative demonstration of a predetermined target sequence by the methods described above, biological and chemical reagents used in the assays must be used in readily determinable quantities sufficient to generate a reproducible, detectable signal in a sensitive assay.

For a quantitative determination, the amount of probe added should be substantially in excess of the highest amount of target sequence expected and incubation should be carried out under conditions such that virtually all target sequences hybridize with probes. By "virtually all" we mean a very high percentage sufficient to impart reproducibility to the assay. In subsequent steps through signal detection, each step should be similarly quantitative. For example, destruction of unbound probes should destroy virtually all of the unbound probes for reproducibility and also to eliminate background noise. Transcription and replication steps should utilize sufficient reagents to be quantitative and should be carried out for set times for the sake of reproducibility.

Often, both qualitative and quantitative assays will include parallel assays of at least a negative control, that is, one not containing target sequence, and at times will also include a series of samples containing known amounts of target sequence, such as a geometrically increasing series.

The present invention is also directed to assay kits useful for the qualitative detection or quantitative determination of at least one specific, predetermined nucleic acid target sequence using probe molecules of this invention. Assay kits will include quantities of one or more probes which comprise at least the three essential sequences described above and at least one additional biologically active molecule, for example, a DNA strand, a ribozyme former, an RNA strand or an enzyme, useful for generating a signal indicative of switch opening. Kits may also include additional reagents such wash solutions, insolubilizing reagents and materials, amplification reagents and detection reagents. Amplification reagents may include enzymes and nucleotides. Detection reagents may include labeled nucleotides and color-forming substrates. Kits designed for research may include plasmids which will enable a researcher to prepare probes according to this invention containing any desired probe sequence.

We claim:

1. A method for the detection of at least one predetermined nucleic acid target sequence in a sample containing nucleic acid and comprising the steps of:
   a) adding to the sample hybridization probes comprising a molecular switch consisting essentially of three oligonucleotide sequences:
      i) a probe sequence of from about 20 to about 60 nucleotides, having a 5' side and a 3' side, which probe sequence is complementary to said target sequence,
      ii) a 5' sequence of from about 10 to about 40 nucleotides, including a first switch sequence of at least about 10 nucleotides, immediately adjacent to and linked to the 5' side of the probe sequence, and
      iii) a 3' sequence of from about 10 to about 40 nucleotides, including a second switch sequence of at least about 10 nucleotides, immediately adjacent to and linked to the 3' side of the probe sequence, said second switch sequence being hybridized with said first switch sequence only when said probe sequence is not hybridized to said target sequence,
   wherein said molecular switch includes a preselected nucleic acid sequence for selectively generating a detectable signal when the probe sequence is hybridized with said target sequence,
   b) specifically hybridizing probes with said target sequence,
   c) destroying the ability of probes which did not hybridize specifically with said target sequence in step b to generate a signal,
   d) generating a signal from probes which did hybridize specifically with said target sequence in step b, and
   e) detecting the signal in order to detect the predetermined nucleic acid target sequence.

2. A method according to claim 1 wherein said probe is a replicatable RNA.

3. A method according to claim 2 wherein step c comprises destroying with a ribonuclease the replicability of probes which did not hybridize specifically with said target sequence and wherein step d comprises exponentially replicating probes which did hybridize specifically with said target sequence.

4. A method according to claim 2 wherein probes hybridized specifically with said target sequence in step b are separated from probes which did not so hybridize prior to performing step d.

5. A method according to claim 1 comprising a quantitative determination of the amount of said target sequence in said sample, wherein the amount of probe added in step a substantially exceeds the maximum number of target sequences expected in said samples, wherein step b proceeds until virtually all target sequences hybridize with probes, wherein step c the replicability of virtually all of the probes which did not hybridize specifically with said target sequence is destroyed, wherein step d is carried out for a predetermined time, and wherein step e is quantitative.

6. A method according to claim 5 additionally comprising performing a parallel assay on a sample which does not contain said target sequence.

7. A method for the detection of at least one predetermined nucleic acid target sequence in a sample containing nucleic acid comprising the steps of
   a) adding to the sample hybridization probes comprising a molecular switch consisting essentially of three oligonucleotide sequence:
      i) a probe sequence of from about 20 to about 60 nucleotides, having a 5' side and a 3' side, which probe sequence is complementary to said target sequence,
      ii) a 5' sequence of from about 10 to about 40 nucleotides, including a first switch sequence of at least about 10 nucleotides, immediately adjacent to and linked to the 5' side of the probe sequence, and
      iii) a 3' sequence of from about 10 to about 40 nucleotides, including a second switch sequence of at least about 10 nucleotides, immediately adjacent to and linked to the 3' side of the probe sequence, said second switch sequence being hybridized with said first switch sequence only when said probe sequence is not hybridized to said target sequence,
   wherein said molecular switch includes a preselected nucleic acid sequence for selectively generating a detectable signal when the probe sequence is hybridized with said target sequence, said detectable signal resulting from exponential replication of replicable RNA,
   b) specifically hybridizing probes with said target sequence,
   c) exponentially replicating the replicatable RNA, and
   d) detecting the replication products in order to detect the predetermined nucleic acid target sequence.

8. A method according to claim 7, wherein said probe is a first DNA strand, comprising the additional step of hybridizing to the second switch sequence of said probe a second DNA strand which is a template for the transcription of a replicatable RNA prior to step c.

9. A method according to claim 7, wherein said probe is a replicatable recombinant RNA, comprising the additional step of separating probes which hybridized with target sequence in step b from probes which did not so hybridize prior to step c, and wherein the replicatable RNA of step c is said replicatable recombinant RNA.

10. A method according to claim 7 wherein said probe is an RNA strand comprising a replicatable RNA sequence extending from said second switch sequence, comprising the additional step of selectively cleaving said replicatable RNA sequence from probes which hybridized with target sequences in step b prior to step c, and wherein the replicatable RNA of step c is said replicatable RNA sequence.

11. A method according to claim 10 wherein the step of cleaving involves ribozyme cleavage.

12. A method according to claim 10 wherein the step of cleaving includes adding a ribonuclease to the sample.

13. A method according to claim 7 comprising a quantitative determination of the amount of said target sequence in said sample, wherein the amount of probe added in step a substantially exceeds the maximum number of target sequences expected in said sample, wherein step b proceeds until virtually all target hybridize with probes, wherein step c is carried out for a predetermined time, and wherein step d is quantitative.

14. A method according to claim 13 additionally comprising performing a parallel assay on a sample which does not contain said target sequence.

15. A method for the detection of at least one predetermined nucleic acid target sequence in a sample containing nucleic acid comprising the steps of
   a) adding to the sample hybridization probes comprising a molecular switch consisting essentially of three oligonucleotides sequences:
      i) a probe sequence of from about 20 to about 60 nucleotides, having a 5' side and a 3' side, which probe sequence is complementary to said target sequence,
      ii) a 5' sequence of from about 10 to about 40 nucleotides, including a first switch sequence of at least about 10 nucleotides, immediately adjacent to and linked to the 5' side of the probe sequence, and
      iii) a 3' sequence of from about 10 to about 40 nucleotides, including a second switch sequence of at least about 10 nucleotides, immediately adjacent to and linked to the 3' side of the probe sequence, said second switch sequence being hybridized with said first switch sequence being when said probe sequence is not hybridized to said target sequence, wherein said molecular switch includes a preselected nucleic acid sequence for selectively generating a detectable signal from an RNA signal generator sequence of said hybridization probe when the probe sequence is hybridized with said target sequence,
   b) specifically hybridizing probes with said target sequence,
   c) cleaving said RNA-signal generator sequence from probes which hybridized with target sequences in step b,
   d) generating an amplified signal using said RNA-signal generator, and
   e) detecting said amplified signal in order to detect the predetermined nucleic acid target sequence.

16. A method according to claim 15 wherein said RNA-signal generator includes an enzyme which generates a color signal.

17. A test kit for performing an assay according to claim 1 comprising a quantity of said probes and an appropriate RNA replicase.

18. A test kit for performing an assay according to claim 7 comprising a quantity of said probes and an appropriate RNA replicase.

19. The method of claim 8 wherein the replicatable RNA is MDV-poly-RNA.

20. The method of claim 8 wherein the second DNA strand includes a promoter sequence for a DNA directed RNA polymerase.

21. The method of claim 20 wherein the exponential replication of step (c) is performed with Q-beta replicase.

22. The method of claim 9 wherein the predetermined target sequence is a gene segment.

23. The method of claim 20 wherein the promoter is for T7 RNA polymerase.

* * * * *

UNITED STATES PATENT AND TRADEMARK OFFICE
CERTIFICATE OF CORRECTION

PATENT NO. : 5,312,728
DATED : May 17, 1994
INVENTOR(S) : Lizardi, et al.

It is certified that error appears in the above-identified patent and that said Letters Patent is hereby corrected as shown below:

Claim 13, Column 17, line 17 - insert "sequences" after the word "target".

Claim 15, Column 18, line 2, change "being" to "only"

Signed and Sealed this

Twenty-third Day of August, 1994

BRUCE LEHMAN

*Attest:*

*Attesting Officer*  *Commissioner of Patents and Trademarks*